United States Patent [19]

Greatbatch

[11] 4,294,256

[45] Oct. 13, 1981

[54] RATE CONTROLLED DIGITAL PACEMAKER

[76] Inventor: Wilson Greatbatch, 5220 Donnington Rd., Clarence, N.Y. 14031

[21] Appl. No.: 57,745

[22] Filed: Jul. 16, 1979

[51] Int. Cl.³ .............................................. A61N 1/36
[52] U.S. Cl. ............................................ 128/419 PT
[58] Field of Search .................. 128/419 PG, 419 PT

[56] References Cited

U.S. PATENT DOCUMENTS 3,830,242   8/1974   Greatbatch .................. 128/419 PT
4,095,603   6/1978   Davies ......................... 128/419 PT Primary Examiner—William E. Kamm
Attorney, Agent, or Firm—Christel, Bean & Linihan

[57] ABSTRACT

An artificial cardiac pacer including a pulse source of relatively high and constant frequency, such as a quartz crystal oscillator, and a frequency divider for converting the source pulses to a lower frequency suitable for application to pacer electrodes for heart stimulation is provided with a pulse rate controller operatively connected to the frequency converter for inhibiting a predetermined number of pulses in each time interval to change the frequency of pulses applied to the pacer electrodes. An external controller operatively coupled to the pulse rate control generates first and second command signals in response to manual selection which are received by the pulse rate control and cause an increase or decrease in the number of pulses inhibited.

11 Claims, 4 Drawing Figures

RATE CONTROLLED DIGITAL PACEMAKER

BACKGROUND OF THE INVENTION

This invention relates to the electronic cardiac pacer art, and more particularly to a new and improved electronic cardiac pacer having stimulation rate control.

Early in the development of electronic cardiac pacemaking there appeared the nonsynchronous pacer which provides fixed rate stimulation, and although the stimulation is not automatically changed in accordance with the body's needs, it has proven effective in alleviating the symptoms of complete heart block. A nonsynchronous pacer, however, has the possible disadvantage of competing with the natural, physiological pacer during episodes of normal sinus conduction.

As a result, the demand-type pacer was developed having the capability that artificial stimuli are initiated only when required and subsequently can be eliminated when the heart returns to the sinus rhythm. The demand pacer solves the problem encountered with the nonsynchronous pacer by inhibiting itself in the presence of ventricular activity but coming "on line" and filling in missed heartbeats in the absence of ventricular activity.

More recently, a cardiac pacer of the demand type was developed wherein pulse generation is locked in timing relation to a source of timing signals which operates at a constant frequency. In this pacer the timing element includes digital clock circuitry of the integrated circuit type, and the pacer encourages the natural heart rate to conform to a precise repetitive signal. In particular, this digital pacer operates from a quartz crystal through a frequency divider chain to give output pulses at a rate of approximately one per second. Such a pacer has a very precise rate which will never change appreciably and will never run away. It would be highly desirable to provide such a pacer having the capability of control of stimulation rate and with such rate changes advantageously being made form an external controller.

SUMMARY OF THE INVENTION

It is, therefore, an object of this invention to provide a new and improved artificial cardiac pacer wherein pulse generation is locked in timing relation to a source of timing signals operating at a constant frequency and having the capability of control of stimulation rate.

It is a further object of this invention to provide such an artificial cardiac pacer wherein the control is effected by instructions provided externally or remotely of the pacer.

It is a further object of this invention to provide such an artificial cardiac pacer which is of the implanted type and wherein the control is commanded or instructed from outside the patient's body.

It is a further object of this invention to provide such an artificial cardiac pacer wherein the control increases or decreases the stimulation rate within fixed limits for purposes of safety.

It is a further object of this invention to provide such an artificial cardiac pacer wherein the control is effected in response to only coded instructions for purposes of safety.

The present invention provides, in combination with an artificial cardiac pacer including a source of pulses having a relatively high and constant frequency and means for converting the high frequency pulses to pulses having a relatively lower frequency suitable for application to pacer electrodes for heart stimulation, pulse rate control means operatively connected to the frequency converting means for blanking or inhibiting a predetermined number of pulses in each time interval to change the frequency of pulses applied to the pacer electrodes and auxiliary control means operatively coupled to the pulse rate control means for determining the number of pulses to be inhibited. The auxiliary control means generates first and second coded command signals for instructing the pulse rate control means to increase or decrease the number of pulses to be inhibited, the pulse rate control means including means responsive only to the coded first and second command signals. The artificial cardiac pacer with the pulse rate control means can be implanted in the patient's body, and the auxiliary control means can be located outside of the patient's body and include manually-operated means for selecting as between the first and second command signals together with a transmitter for applying the command signals externally of the patient's body which command signals then are received by a pickup device within the patient's body and transmitted by electrical conductor means to the pulse rate control means.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENT

Figure 1:
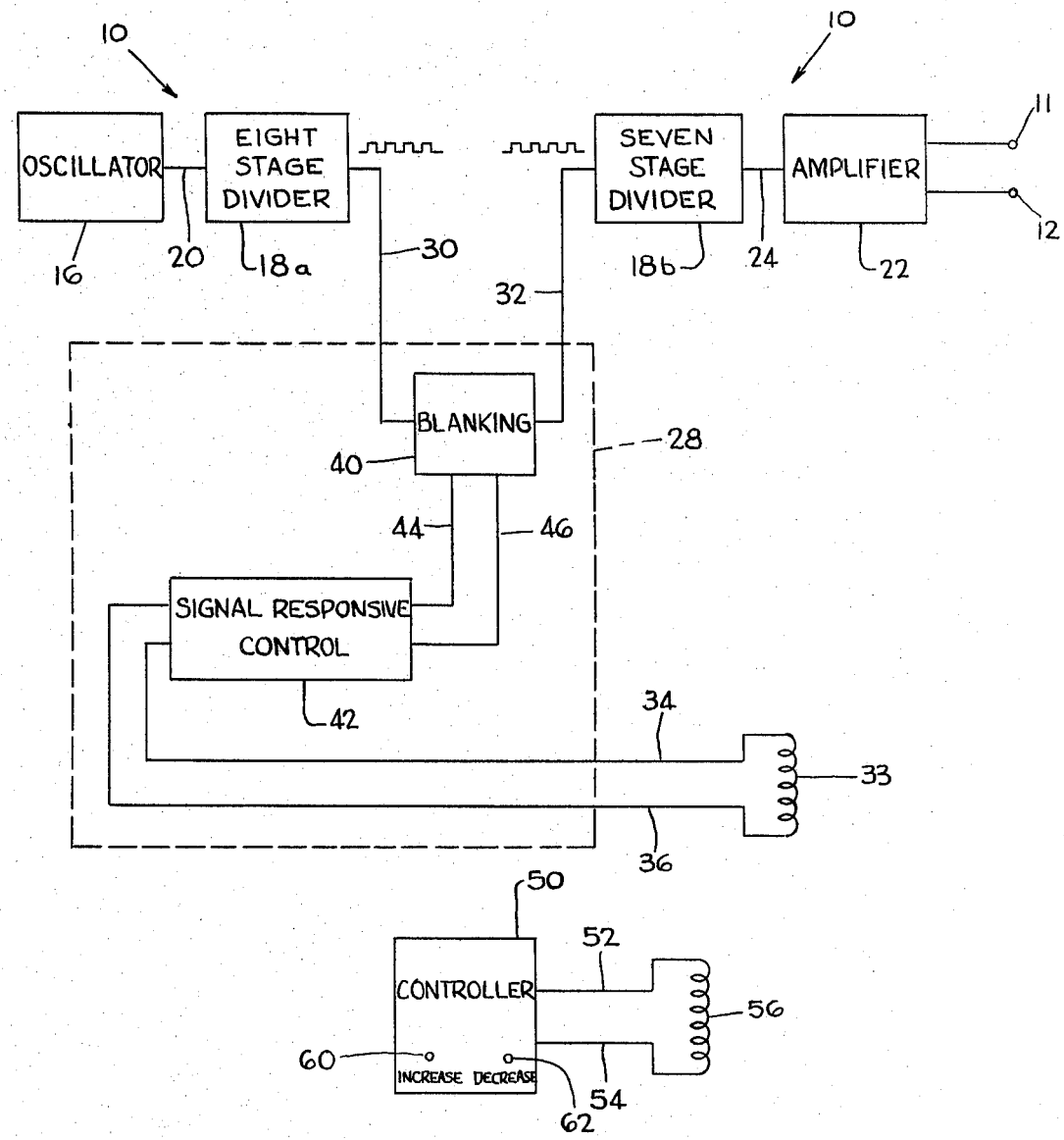
FIG. 1 is a block diagram of an artificial cardiac pacer system according to the present invention.

A digital pacemaker utilizing a quartz crystal as a very precise control of heart rate is described in U.S. Pat. No. 3,870,050 issued Mar. 11, 1975, the disclosure of which hereby is incorporated by reference. In the pacer described in that patent a quartz crystal operates through a frequency divider chain to give an output pulse approximately once per second. In particular, a quartz cyrstal oscillator output of 16,384 hertz is divided down by binary digital dividers to a pulse rate of 2 hertz in 13 steps as follows: 16,384, 8,192, 4,096, 2,048, 1024, 512, 256, 128, 64, 32, 16, 8, 4 and 2 hertz. Such a pacer has a very precise rate which would never change appreciabley and would never run away.

It would be highly desirable to provide such a pacemaker having the additional capability of control of stimulation rate and, in addition, providing such control from outside of the patient's body when the pacemaker is implanted. In accordance with the present invention, an external control is superimposed on the frequency source in the form of blanking a certain number of beats at an intermediate step in the frequency divider. In particular, at the eighth step in the frequency divider where the frequency is 64 hertz, blanking one pulse each second will cause the pulses applied to the pacer electrodes to be decreased in interval by one pulse in 64 or approximately 1.5 percent at 64 pulses or 3 percent at 32 pulses, when the remaining 32 pulses are blanked. This is because the pulse train running unblanked gives 2 hertz or 120 pulses/second and with 32 pulses blanked at 64 the rate would be 60 pulses/second. As each additional pulse at the eighth stage in the frequency divider is inhibited, the stimulation rate will be decreased by another 3 percent. For example, with 32 pulses being inhibited, the heart rate would be 60 beats per minute. If an additional 8 pulses were inhibited, 24 pulses would be left providing a heart rate of 45 beats per minute. Thus, each application of an increase instruction signal will increase the heart stimulation rate by 3 percent, and each application of a decrease instruction signal will decrease the heart rate by a similar amount, the foregoing being within predetermined limits for purposes of safety. In other words, in order to vary the stimulation rate about 60 pulses/minute, i.e. 30 pulses/minute to 120 pulses/minute, it is necessary to have a 13 step divider with the eigth step at 64 pulses/second, blanked half the time. At 60 pulses/minute the eighth step would have 32 steps blanked, i.e. it would count 32 and then rest inactive for the last 32. This would give 60 pulses/minute with 32 steps blanked, 63 pulses/minute with 31 steps blanked and 57 pulses/minute with 33 steps blanked, a variation of about 3 percent. The instructions can be provided by an external controller in the form of a device inductively coupled to a receiving coil in the implanted pacemaker, and the controller operates to apply instruction signals to the pacer via the induction path. Alternatively, the instructions could be provided directly via ECG leads on the patient's body. The device can include two manually operated switch buttons identified as increase and decrease and constructed so that depressing the first button will increase the heart rate about 3 percent each time it is pressed and depressing the second button will decrease the heart rate about 3 percent each time it is pressed. The heart rate will then remain at the newly instructed rate even after the external device is disconnected.

Referring now to FIG. 1, the system of the present invention includes a cardiac pacer 10 comprising electrode means adapted to be operatively connected to a patient's heart. The system shown includes a pair of electrodes 11, 12 at least one of which is surgically placed in contact with the heart of the patient. In particular, negative electrode 11 would be placed surgically in contact with the ventricle of the patient's heart and electrode 12, which can function as an indifferent or reference electrode, could be subcutaneously implanted at another part of the patient's body. Alternatively, electrode 12 also can be placed in contact with the patient's heart. Electrodes 11, 12 are connected to the circuitry of the cardiac pacer by leads or wires which are enveloped by a moisture-proof and human body reaction-free material such as silicone rubber or suitable plastic.

The cardiac pacer 10 further comprises a source providing an output train of electrical pulses having a constant frequency and including a pulse source 16 such as an oscillator which provides output pulses at relatively high frequency and means in the form of a divider 18 for converting the high frequency pulses to pulses having a lower frequency suitable for heart stimulation. Divider 18 is in the form of a binary electronic frequency divider which divides the frequency of the pulse sequentially down to a relatively lower frequency corresponding to the desired fixed stimulation rate for the heart. In the system shown, divider 18 is in the form of a first component 18a having an input connected by line 20 to the output of oscillator 16 and an output, and component 18 includes eight stages of frequency division. The divider includes a second component 18b which includes five stages of frequency division. The divider 18 shown in FIG. 1 as including the two components 18a, 18b can be in the form of two separate dividers, or alternatively a single divider with operative connection to an intermediate stage, in a manner which will be described. The cardiac pacer 10 further comprises means for coupling the train of pulses from the source to the electrode means in the form of a pacer amplifier 22 and related circuitry having an input connected by line 24 to the output of divider component 18b and an output connected to electrodes 11, 12. Amplifier 22 also shapes each pulse into a pacemaker output pulse of about onee millisecond duration. Electrical energy for operating oscillator 16, divider 18 and amplifier 22 is obtained from a suitable source such as a battery (not shown) in a known manner. The cardiac pacer including electrodes 11, 12 source 16, divider 18 and amplifier 22 is similar to the pacer described in U.S. Pat. No. 3,870,050 referenced hereinabove.

In accordance with this invention there is provided pulse rate control means generally designated 28 operatively connected to the frequency converting means or divider 18 for blanking a predetermined number of pulses coupled to the electrodes 11, 12. In the system shown pulse rate control means 28 is operatively connected to an intermediate stage of the converting means 18, in particular between the components 18a and 18b shown in FIG. 1 which is after the eighth stage of frequency division. Thus, the output of divider component 18a is connected by a line 30 to pulse rate control means 28, and pulse rate control means 28 is connected by lead 32 to the input of divider component 18b. In the system shown a signal receiving means in the form of a pickup coil 33 in the implanted pacemaker is connected by electrical leads 34 and 36 to pulse rate control means 28 for transmitting command or instruction signals to the pulse rate control means in a manner which will be described. The pulse rate control means 28 includes means designated 40 for generating blanking pulses of a predetermined number during each time interval of the train of pulses in converting means 18 and in synchronism with the train of pulses together with means for applying the blanking pulses to the train of pulses in the converting means 18. The means 40 also functions to increase or decrease the number of blanking pulses, i.e. the number of pulses in the train which are blanked, in response to appropriate commands and to maintain application of the predetermined number of blanking pulses by means of suitable memory capability until another command is received. The pulse rate control means 28 further comprises signal responsive means 42 for controlling the number of pulses in the train of converter 18 which are to be blanked. The signal responsive means 42 includes frequency selective networks and determines whether the number of pulses to be blanked, i.e. the number of blanking pulses generated, and hence the ultimate pulse rate, is to be increased or decreased. The output of the signal responsive means 42 is connected by lines 44, 46 to the blanking pulse generating means 40. Lines 34 and 36 leading from pacer electrodes 11 and 12, respectively, are connected to the input of network 42. As a result, command or instruction signals picked up by the transducer or coil 33 are transmitted by leads 34, 36 to the input of the network 42 for decoding and other appropriate operations as will be described in detail presently.

The system of the present invention further comprises auxiliary control means 50 operatively coupled to the pulse rate control means 28 for changing the number of pulses to be blanked. In the system shown, the auxiliary control means is connected by lines 52 and 54 to a signal transmitting means in the form of a transmitting coil 56 adapted to be coupled inductively to the pickup coil 33 of the implanted pacemaker. Such inductive coupling is through the region of the patient's body adjacent the implanted pacemaker in a known manner. The auxiliary control means 50 includes manually operated means in the form of switch control buttons 60 and 62 for initiating or commanding rate change instructions to the cardiac pacer system. In particular, manually depressing the button 60 will result in the rate of stimulating pulses applied by electrodes 11, 12 to the heart to be increased about 3 percent each time the button 60 is pressed. Similarly, depressing button 62 will cause the rate of stimulating pulses applied by electrodes 11, 12 to the heart to be decreased by about 3 percent each time the button 62 is depressed. When the auxiliary controller 50 is disconnected from the patient the cardiac pacer will continue to supply stimulating pulses at the new rate.

By way of illustration, manual operation of the switch button 60 provides a signal in the form of a coded burst such as a 0.15 second chain of a predetermined number of 600 hertz pulses which are transmitted by conductors 52, 54 to the transmit coil 56 operatively associated with the patient. The signal is sensed or received by pickup coil 33 operatively associated with the pacemaker and transmitted by lines 34, 36 to the network 42. The network 42, in turn, is constructed to respond to this signal only if the chain of pulses is precisely at a frequency of 600 hertz, the amplitude is within a preselected limited range, and the correct number of pulses is received. If these conditions are satisfied, network 42 causes the component 40 to generate a blanking pulse in a manner which will be described. Furthermore, each time that the button 60 is depressed and the foregoing conditions are satisfied, one less blanking pulse will be generated by the component 40. Similarly, if button 62 is depressed the auxiliary control means 50 will generate a coded burst in the form of a 0.15 second train of a predetermined number of pulses having a frequency of 900 hertz applied by lines 52,54 to transmit coil 56 operatively associated with the patient. This coded signal is sensed or received by the pickup coil 33 operatively associated with the pacemaker and transmitted by lines 34,36 to the network 42. The network, in turn, will respond only if the chain of pulses has a frequency of precisely 900 hertz, the amplitude is within a preselected limited range and the correct number of pulses is received. These conditions being satisfied, the network 42 will cause the component 40 to add one blanking pulse from that applied to the pulse train in the converting means 18. Furthermore, each time the button 62 is depressed and the foregoing conditions are satisfied, another blanking pulse will be added. The foregoing will result in a decrease in the rate of stimulating pulses applied by electrodes 11, 12. The foregoing can occur to a minimum limit of 30 beats per minute which is the condition when only 16 pulses per second are passed by the eighth stage of the frequency dividing means 18 with 48 (16+32) pulses being blanked or inhibited. Similarly, this process can occur up to a maximum limit of 120 beats/minute, which is the condition when 64 pulses per second are being passed by the eighth stage, with no pulses being blanked. Also, similar blanking could alternatively be accomplished at any divider stage prior to the eighth stage, and any one of a number of schemes, well known to those skilled in the art, could be employed to generate the blanking pulses.

Figure 2:
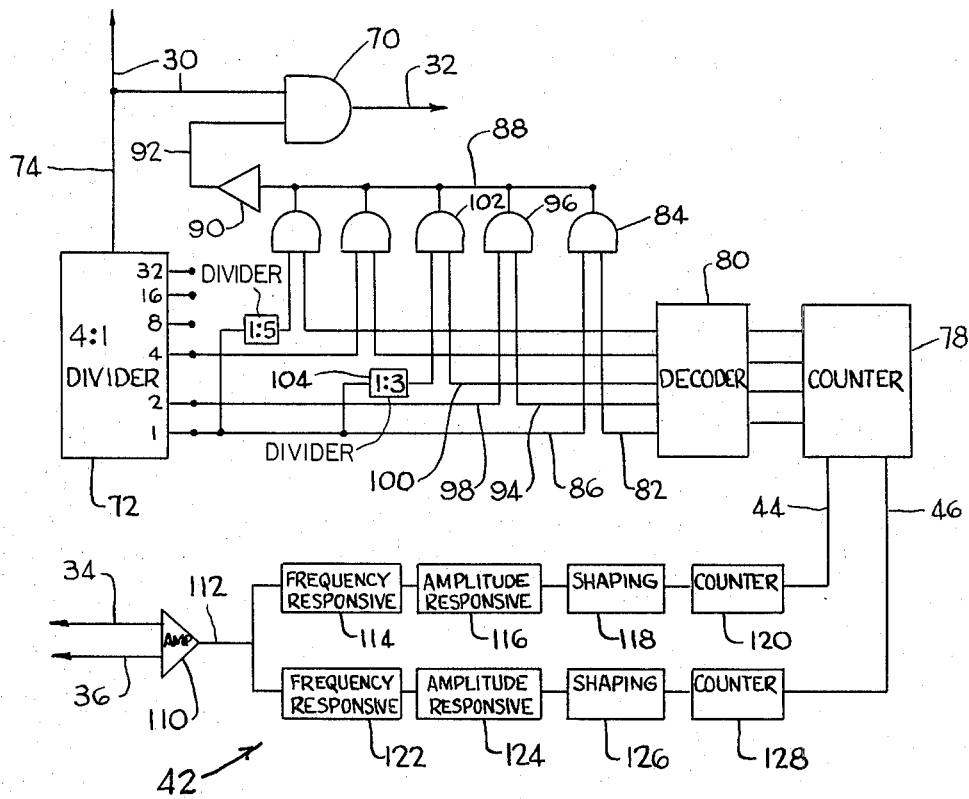
FIG. 2 is a schematic block diagram of the pulse rate control means of the system of FIG. 1.

FIG. 2 illustrates one form of circuitry which can be employed to implement the pulse rate control means 28 of the system of FIG. 1. The pulse rate control means includes means for generating a predetermined number of blanking or inhibit pulses during each time interval of the train of pulses in converting means 18 and in synchronism with the train of pulses therein and it further includes means for applying the blanking or inhibit pulses to the train of pulses in the converting means. The circuit shown in FIG. 2 includes gate means in the form of an AND gate 70 having a pair of inputs, one of which is connected to line 30 from the output of the frequency divider component 18a, and an output which is connected to line 32 leading to the input of the other frequency divider component 18b. The circuit further includes frequency dividing means in the form of a 4:1 binary divider 72 having an input connected by line 74 to line 30. Since the output of the frequency converting stage 18a is 64 pulses per second, the six outputs of the divider 72 are labeled in FIG. 2 with the appropriate frequency value. As a result, pulse trains having these various frequencies are available at the outputs of the binary divider 72 which are in synchronism with the train of pulses traveling through the pacemaker frequency converter 18. In other words, each output of divider 72 provides a train of pulses of different frequencies in synchronism with the train in divider 18 which can be employed as blanking or inhibit pulses, and the particular output, and hence number of inhibit pulses, is selected by the following arrangement.

The circuit of FIG. 2 further comprises a conventional binary counter 78 wherein lines 44 and 46 from the frequency selective component 42 are connected to the count up and count down terminals, respectively, of the counter 78. The counter shown has four output terminals providing 16 separate logical quantities corresponding to discrete count values. These, in turn, are connected by four conductors to the input of a logic decoder network 80 for converting the discrete count values into output signals appearing on a particular output terminal. In the circuit shown there are only five output terminals leading from the decoder 80 but it is to be understood that a total of sixteen output terminals can be provided. The network 80 includes suitable gate circuitry readily apparent to those skilled in the art whereby the binary work or quantity on the four input lines to decoder 80 is transformed into a logical signal on only one of the output terminals of network 80. In other words, each of the sixteen possible input quantities to decoder 80 will result in a logical one output signal on only a particular one of the maximum number of output terminals. These logical output signals, in turn, are utilized to control application of the different output pulse trains from divider 72 by the following arrangement.

The output terminal of decoder 80 corresponding to count number one from counter 78 is connected by a line 82 to one input of an AND gate 84, the other input of which is connected by a line 86 to the lowest frequency output of divider 72 which corresponds to one pulse per second. Thus, when one signal applied by line 44 to the up count terminal of counter 78 is received, the result is that the pulse train from divider 72 corresponding to one pulse per second is transmitted through AND gate 84, line 88, inverter 90, and line 92 to the input of AND gate 70. The inverter 90 causes an inhibit signal of one pulse per second to be applied to AND gate 70. So long as no additional signal is received by counter 78 the decoder 80 will continue to enable the AND gate 84 so that during succesive periods the pulse train of one pulse per second appearing on line 86 will be transmitted to line 88 and ultimately as an inhibit signal to AND gate 70 at the rate of one inhibit pulse per second. Should another signal be received on line 44, counter 78 changes its state to a count of two which is transformed by decoder 80 to a logical one output signal appearing only on line 94 which is connected to one input of an AND gate 96, the other input of which is connected by a line 98 to the output terminal of divider 72 having a pulse train with frequency of two cycles per second. As a result, an inhibit signal having a rate of two pulses per second is applied to the input of AND gate 70. Should another pulse appear on line 44 the state of counter 78 is changed to a binary output of three which is transformed by decoder 80 to a logical one output signal only on the line 100 leading to the input of an AND gate 102. In order to provide an output of three cycles per second from divider 72, a 1:3 frequency multiplier 104 is connected between line 86 and the other input of AND gate 102. By proceeding through a similar analysis, it will be seen that as successive signals are applied on line 44 to counter 78 to increase the output count, there is a corresponding increase in the frequency of the pulse train appearing on line 88 which, in turn, results in a corresponding increase in the frequency of inhibit pulses applied to the input of AND gate 70. Furthermore, proceeding with the foregoing example, should a signal next appear on line 46, the counter will count down decreasing its count by one quantity which according to the foregoing example would bring the output down to a binary two which is transformed by the decoder 80 to a logical one output signal only on the line 94 leading to AND gate 96 with the result that the output pulse train from divider 72 having a frequency of two cycles per second is applied through line 98 to the other input of AND gate 96. As a result, the frequency of the inhibit pulses applied to AND gate 70 decreases from three pulses per second to two pulses per second. By proceeding through a similar analysis, it will be seen that as successive signals are applied on line 46 to counter 78 to decrease the output count, there is a corresponding decrease in the frequency of the pulse train on line 88 which, in turn, results in a corresponding decrease in the frequency of inhibit pulses applied to the input of AND gate 70.

Figure 4:
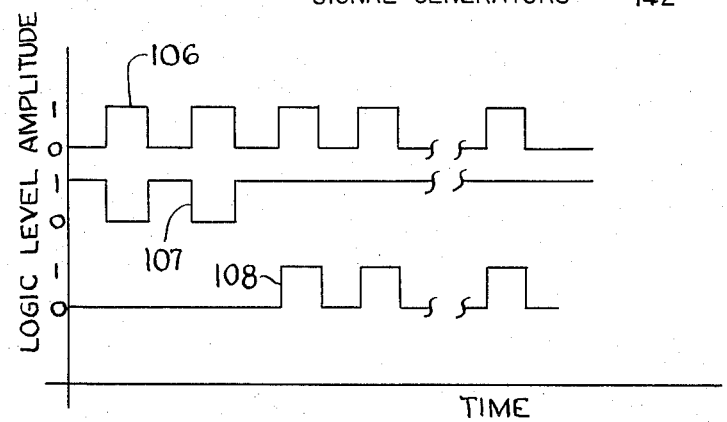
FIG. 4 includes waveforms further illustrating the operation of the cardiac pacer system of the present invention.

Thus, a train of pulses appear on line 88 corresponding to one of the various outputs of frequency divider 72 is selected by the particular state of the counter 78. The counter state, in turn, is determined by the nature of the signals appearing on lines 44, 46. The pulses on line 88 each have a logical one value, and since gate 70 is of the AND type, the inverter 90 converts those pulses to a logical zero value appearing on line 92. These logical zero pulses serve as inhibit pulses so that anytime one is present this will prevent transmission of a pulse from line 30 through gate 70 to line 32. This is further illustrated in the waveform of FIG. 4. In particular, waveform 106 is the pulse train on line 30 leading from the output of frequency divider component 18a and depicted for a time period of one second. This train includes 32 pulses during each one second time period, five of which are shown in FIG. 4 for convenience in illustration. These pulses are applied to one input of AND gate 70 in the circuit of FIG. 2. Waveform 107 is the train of inhibit pulses on line 92 which is applied to the other input of AND gate 70. Waveform 107 corresponds to the previous example wherein AND gate 96 is enabled to apply an inhibit signal having a rate of two pulses per second to the input of AND gate 70. Waveform 108 is the output of AND gate 70 on line 32 leading to frequency divider component 18b. In the present illustration this is a train of pulses having a frequency of 30 pulses per second.

The pulse rate control means 28 further includes signal responsive means 42 which cooperates with the foregoing circuitry including counter 78 to control the number of pulses in the pulse train of frequency converter 18 which are to be inhibited. As shown in FIG. 2, lines 34 and 36 from the pickup coil 33 are connected to the input terminals of a conventional preamplifier 110. Of course, if the signals on lines 34, 36 are of sufficient magnitude to be processed by the remaining circuitry, the amplifier 110 can be omitted. The output of amplifier 110 is available on line 112 which, in turn, is connected through two signal responsive branch networks to the lines 44 and 46 connected to the input of counter 78. The first branch includes the series combination of a frequency responsive network 114, an amplitude responsive network 116, a wave-shaping network 118, and a counter 120. Thus, a signal received by this branch from line 112 first must be of a proper frequency to be transmitted through component 114 and must be of a particular amplitude to be transmitted through component 116. Assuming thse conditions to be satisfied, the transmitted signal is shaped if necessary by the component 118 and is applied to the input of a counting means 120 which is designed to produce an output on line 44 only in response to a predetermined number of input signals. Likewise, the other branch comprises the series combination of a frequency responsive network 122, an amplitude responsive network 124, a wave shaping network 126, and a counting means 128, the output of which is connected to line 46. Network 122 is responsive only to signals of a particular frequency which will be different from the frequency of network 114. Component 124 functions to transmit only those signals of a predetermined amplitude which may or may not be similar to the amplitude transmitted by component 116 in the other branch. The output of network 124 is transmitted through a wave shaping network if necessary to the input of counter 128 which functions to provide an output signal on line 46 only in response to a predetermined number of signals being applied to the input thereof. This predetermined number may or may not be equal to the number necessary to cause counter 120 in the other branch to provide an output signal.

Figure 3:
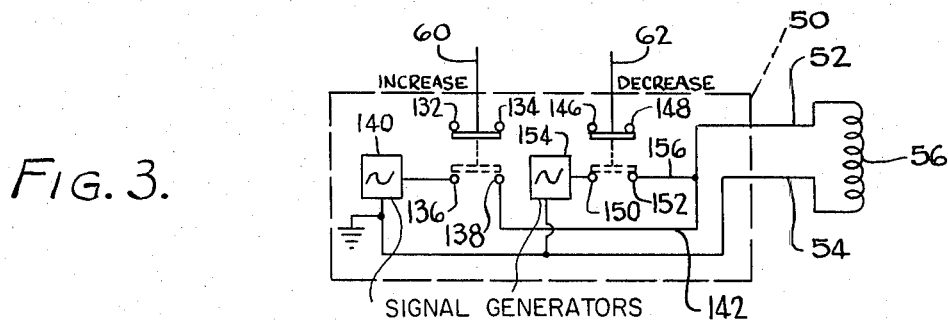
FIG. 3 is a schematic block diagram of the auxiliary control means of the system of FIG. 1.

FIG. 3 illustrates one exemplary form of the auxiliary control means 50 of the system of FIG. 1. A first switch includes operator element or push button 60 which normally bridges a pair of switch contacts 132, 134. Switch contacts 132, 134 are not connected electrically in the system of FIG. 1 but instead serve as mechanical stops for operator element 60. Depressing or otherwise operating the switch button 60 moves it from a position bridging contacts 132, 134 to a position bridging a second pair of contacts 136, 138. Contact 136 is connected to the output of a signal generator 140 which provides output signals coded in terms of frequency, amplitude and number of pulses. The branch in the network of FIG. 2 connected to line 46 is responsive to these coded signals. Contact 138 is connected by a line 142 to the conductor 52 whereby in this position of switch button 60 the output of signal source or generator 140 is applied by line 52 to one terminal of transmitting coil 56. The auxiliary control means further comprises another switch including operator element 62 which normally bridges a pair of switch contacts 146,148. Switch contacts 146, 148 are not connected electrically in the system but instead serve as mechanical stops for operator element 62. Depressing or otherwise moving switch button 62 causes it to move to a position bridging a second pair of switch contacts 150, 152. Switch contact 150 is connected to the output of a signal generator 154 which produces signals coded in terms of frequency, amplitude and number of pulses. The branch in the network of FIG. 2 connected to line 44 is responsive to these coded signals. Switch contact 152 is connected by a line 156 to conductor 52 which is connected to the one terminal of transmitting coil 56. The other terminal of coil 56 is connected by line 54 to a circuit ground or reference which also is connected to the signal generators 140,154. Thus, when neither of the switch buttons 60 or 62 is depressed, the transmitting coil 56 is disconnected from both signal generators 140 and 154. When either of the switch buttons 60 or 62 is depressed, however, an electrical circuit is completed from the corresponding one of the signal generators 140 or 154 through the conductor 52 to one terminal of coil 56 and from the other coil terminal through line 54 to the circuit ground or reference. Thus, coded signals from the signal generator are transmitted, i.e. inductively coupled, through the patient to the pulse rate control means. Such coding also includes instructions that the coded signal train is transmitted only once each time switch buttons 60 or 62 are depressed.

It is therefore apparent that the present invention accomplishes its intended objects. The cardiac pacemaker of the present invention generates stimulating pulses which are locked in timing relation to a source of timing signals operating at a constant frequency and wherein the stimulation pulse rate is controlled by instructions provided externally or remotely of the pacemaker. When the pacemaker is of the implanted type, the control advantageously is commanded or instructed from outside of the patient's body. The control is performed in a manner which increases or decreases the stimulation rate within fixed limits for purposes of safety, and the control is effected in response to only coded instructions for purposes of safety.

While a single embodiment of the present invention has been described in detail, this is done for the purpose of illustration, not limitation.

I claim:

1. In combination with a cardiac pacer comprising electrode means adapted to be operatively connected to a patient's heart for applying stimulating pulses thereto, a source providing an output train of electrical pulses having a constant frequency and including oscillator means providing a train of output pulses at a relatively high frequency and means for converting said high frequency pulses to pulses having a lower frequency suitable for heart stimulation comprising a first component including a plurality of frequency divider stages having an output and having an input connected to said oscillator output and a second component including a plurality of frequency divider stages having an input and an output, and coupling means connected to the output of said second component of said frequency converting means for coupling said lower frequency pulses to said electrode means;

(a) pulse rate control means connected in series between said output of said first component of said frequency converting means and said input of said second component of said frequency converting means, said pulse rate control means comprising means for providing a path for said train of pulses from the output of said first component to the input of said second component of said frequency converting means, blanking pulse generating means having an input and an output and connected in synchronized relation to said output of said first frequency converting means for generating blanking pulses of a number determined by signal conditions at said input of said generating means during each time interval of said train of pulses and in synchronism with said train of pulses, and means for connecting the output of said blanking pulse generating means in controlling relation to said path providing means for preventing transmission of those pulses in the train which coincide in time with said number of blanking pulses to change the rate of stimulating pulses coupled to said electrode means for application to the heart by an amount determined by the number of blanking pulses;

(b) command signal responsive control means connected to said pulse rate control means for controlling the number of blanking pulses to be applied to said train of pulses in said path, said command signal responsive control means including means connected to said input of said blanking pulse generating means and responsive only to a first command signal for causing said blanking pulse generating means to increase the number of blanking pulses generated during each time interval of said train of pulses by an amount determined by said first command signal to decrease the rate of stimulating pulses applied to the heart and means connected to said input of said blanking pulse generating means and responsive only to a second command signal for causing said blanking pulse generating means to decrease the number of blanking pulses generated during each time interval of said train of pulses by an amount determined by said second command signal to increase the rate of stimulating pulses applied to the heart; and (c) auxiliary control means adapted to receive at least two instruction inputs at a location physically separate from said cardiac pacer and operatively coupled to said command signal responsive means for generating said first and second command signals to change the rate of stimulating pulses applied by said electrode means to the heart, said auxiliary control means including means responsive to one of said instruction inputs for generating said first command signal having a given characteristic and means responsive to the other of said instruction inputs for generating said second command signal having a different characteristic.

2. The combination according to claim 1, wherein said auxiliary control means includes manually operated means for selecting between said first and second command signals.

3. The combination according to claim 1, wherein said auxiliary control means is adapted to be located external to the body of the patient and includes signal transmitting means, wherein said command signal responsive means includes signal receiving means, and wherein said cardiac pacer, pulse rate control means and command signal responsive means are adapted to be implanted in the body of a patient, said signal transmitting adapted to send signals through the patient's skin for reception by said signal receiving means.

4. The combination according to claim 3, wherein said transmitting means comprises a coil adapted to be located outside the patient's body and said receiving means comprises a coil adapted to be located within the patient's body.

5. The combination according to claim 1, wherein said path providing means of said pulse rate control means comprises gate means having a single output connected to the input of said second component of said frequency converting means and having a pair of inputs, one of said inputs connected to the output of said first component of said frequency converting means and the other of said inputs connected to said blanking pulse generating means, said gate allowing transmission of said train of pulses from said one input to said output in response to the absence of blanking pulses and preventing transmission of those pulses in the train which coincide in time with blanking pulses present on said other input.

6. The combination according to claim 5, wherein said means for generating blanking pulses comprises:
(a) means for generating a plurality of blanking pulse trains, said blanking pulse trains differing in number of pulses and the pulses of said blanking trains being in synchronism with the pulses of said train in said path between said first and second components of said frequency converting means; and
(b) circuit means connected to said blanking pulse train generating means and connected in controlled relation to said command signal responsive control means for selecting a particular one of said generated blanking pulse trains as determined by operation of said command signal responsive control means.

7. The combination according to claim 6, wherein said circuit means comprises a first input, means for selecting blanking pulse trains of progressively increasing number of pulses in response to signals successively applied to said first input, a second input, and means for selecting blanking pulse trains of progressively decreasing number of pulses in response to signals successively applied to said second input and wherein said command signal responsive control means comprises a first output connected to said first input of said circuit means for applying thereto control signals each commanding selection of blanking pulse trains of increasing number of pulses and a second output connected to said second input of said circuit means for applying thereto control signals each commanding selection of blanking pulse trains of decreasing number of pulses.

8. The combination according to claim 7, wherein said circuit means includes means for maintaining application of the selected blanking pulse train until another control signal is applied to one of said inputs of said circuit means.

9. The combination according to claim 7, wherein said auxiliary control means includes first input means generating a first command signal having a given characteristic and second input means generating a second command signal and wherein said command signal responsive control means includes means responsive only to said first command signal for applying a control signal to said first input of said circuit means to select a blanking pulse train of increased number of pulses and means responsive only to said second command signal for applying a control signal to said second input of said circuit means to select a blanking pulse train of decreased number of pulses.

10. The combination according to claim 9, wherein said circuit means of said blanking pulse generating means includes means having a plurality of different states selected by successive application of signals to said first and second inputs of said circuit means so that separate control signals applied to said inputs of said circuit means in response to separate operation of said first and second input means of said auxiliary control means cause incremental selection of blanking pulse trains of progressively increasing or decreasing number of pulses.

11. The combination according to claim 10, further including manually operated means for selecting between said first and second input means of said auxiliary control means.

* * * * *